United States Patent
Eguchi et al.

(10) Patent No.: US 10,034,941 B2
(45) Date of Patent: *Jul. 31, 2018

(54) IRON-SALEN COMPLEX

(71) Applicants: IHI Corporation, Tokyo (JP); Yoshihiro Ishikawa, Tokyo (JP)

(72) Inventors: Haruki Eguchi, Tokyo (JP); Yoshihiro Ishikawa, Tokyo (JP)

(73) Assignees: IHI CORPORATION, Tokyo (JP); Yoshihiro Ishikawa, Tokyo (JP)

( * ) Notice: Subject to any disclaimer, the term of this patent is extended or adjusted under 35 U.S.C. 154(b) by 148 days.

This patent is subject to a terminal disclaimer.

(21) Appl. No.: 14/990,981

(22) Filed: Jan. 8, 2016

(65) Prior Publication Data

US 2016/0193337 A1    Jul. 7, 2016

Related U.S. Application Data

(63) Continuation of application No. 12/146,624, filed on Jun. 26, 2008, now abandoned.

(30) Foreign Application Priority Data

Dec. 28, 2007 (JP) .................. 2007-338928

(51) Int. Cl.
| | |
|---|---|
| *A61B 5/055* | (2006.01) |
| *A61K 41/00* | (2006.01) |
| *A61K 49/10* | (2006.01) |
| *A61K 49/12* | (2006.01) |
| *C07D 211/58* | (2006.01) |
| *C07F 15/02* | (2006.01) |
| *C07H 21/04* | (2006.01) |
| *C07J 1/00* | (2006.01) |
| *A61N 2/00* | (2006.01) |
| *A61K 47/54* | (2017.01) |

(52) U.S. Cl.
CPC ........ *A61K 41/0052* (2013.01); *A61K 47/547* (2017.08); *A61K 49/103* (2013.01); *A61K 49/106* (2013.01); *A61K 49/122* (2013.01); *A61N 2/002* (2013.01); *C07D 211/58* (2013.01); *C07F 15/025* (2013.01); *C07H 21/04* (2013.01); *C07J 1/00* (2013.01)

(58) Field of Classification Search
CPC .... A61K 41/00; A61K 41/0052; A61K 49/00; A61K 49/106; A61K 49/122; A61K 49/103; A61K 47/48076; A61K 47/547; A61N 2/002; C07H 21/04; C07J 1/00; C07D 233/54; C07D 265/06; C07D 211/58; C07F 15/025
USPC .... 424/1, 1.11, 1.65, 1.8, 9.1, 9.2, 9.3, 9.36; 514/1, 1.1; 544/88; 548/335
See application file for complete search history.

(56) References Cited

U.S. PATENT DOCUMENTS

| | | | |
|---|---|---|---|
| 4,727,068 A | 2/1988 | Abrams et al. | |
| 4,828,941 A | 5/1989 | Sterzel | |
| 4,871,716 A | 10/1989 | Longo et al. | |
| 5,705,195 A | 1/1998 | Volkonsky et al. | |
| 6,162,469 A | 12/2000 | Atarashi et al. | |
| 6,172,268 B1 | 1/2001 | Tohma et al. | |
| 6,200,547 B1 | 3/2001 | Volkonsky et al. | |
| 6,344,516 B1 | 2/2002 | Ikeda et al. | |
| 8,246,975 B2 * | 8/2012 | Eguchi | A61K 31/282 423/22 |
| 8,933,118 B2 * | 1/2015 | Ishikawa | C07C 251/24 514/492 |
| 9,005,757 B2 * | 4/2015 | Ishikawa | C07C 251/24 128/899 |
| 9,282,923 B2 * | 3/2016 | Ishikawa | C07C 251/24 |
| 9,434,880 B2 * | 9/2016 | Ishikawa | C09K 15/326 |
| 9,505,732 B2 * | 11/2016 | Ishikawa | A61K 31/135 |
| 9,592,219 B2 * | 3/2017 | Ishikawa | C07C 251/08 |

(Continued)

FOREIGN PATENT DOCUMENTS

| | | |
|---|---|---|
| CA | 2113245 A1 | 7/1994 |
| EP | 0800829 A1 | 10/1997 |

(Continued)

OTHER PUBLICATIONS

Alexiou et al., "Locoregional Cancer Treatment with Magnetic Drug Targeting", Cancer Research, Dec. 1, 2000, 60:6641-6648.

(Continued)

*Primary Examiner* — D L Jones
(74) *Attorney, Agent, or Firm* — Drinker Biddle & Reath LLP

(57) ABSTRACT

The present invention provides a drug delivery system that overcomes conventional technical problems and that is readily put to practical use. Iron-salen complexes represented by General Formula (I) below. The invention renders iron-salen complexes magnetic, which can thus be used as drugs that can be delivered to affected areas in the body using the inherent magnetic properties of the drug without employing carriers composed of magnetic substances as has been done hitherto.

[C1]

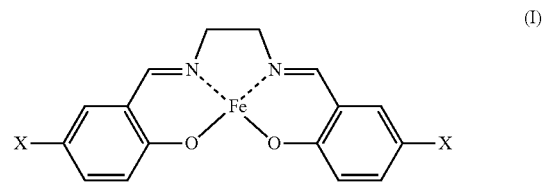

(I)

4 Claims, 6 Drawing Sheets

(56) References Cited

U.S. PATENT DOCUMENTS

| | | |
|---|---|---|
| 2004/0059107 A1 | 3/2004 | Malfroy-Camine et al. |
| 2005/0096260 A1 | 5/2005 | Ueno et al. |
| 2009/0169484 A1 | 7/2009 | Eguchi et al. |
| 2009/0285759 A1 | 11/2009 | Ishikawa et al. |
| 2009/0311163 A1 | 12/2009 | Eguchi et al. |

FOREIGN PATENT DOCUMENTS

| | | |
|---|---|---|
| EP | 1097711 A2 | 5/2001 |
| EP | 1114836 A1 | 7/2001 |
| EP | 1007533 B1 | 6/2005 |
| JP | S49-13317 A | 2/1974 |
| JP | S49-13316 A | 2/1975 |
| JP | S62-174014 A | 7/1987 |
| JP | S62-192383 A | 8/1987 |
| JP | H03-21319 A | 1/1991 |
| JP | H05-45932 A | 2/1993 |
| JP | H05-23276 A | 4/1993 |
| JP | H05-216967 A | 8/1993 |
| JP | H07-149799 A | 6/1995 |
| JP | H07-296045 A | 11/1995 |
| JP | H08-506111 A | 7/1996 |
| JP | H09-291145 A | 11/1997 |
| JP | H09-328438 A | 12/1997 |
| JP | H09-329602 A | 12/1997 |
| JP | H10-310796 A | 11/1998 |
| JP | H11-006825 | 1/1999 |
| JP | H11-507646 A | 7/1999 |
| JP | 2930263 B2 | 8/1999 |
| JP | H11-217385 A | 8/1999 |
| JP | 2000-269013 A | 9/2000 |
| JP | 2001-010978 A | 1/2001 |
| JP | 2002-500177 A | 1/2002 |
| JP | 2002-093606 A | 3/2002 |
| JP | 2002-226678 A | 8/2002 |
| JP | 2004-514724 A | 5/2004 |
| JP | 2004-522971 A | 7/2004 |
| JP | 2004-239685 A | 8/2004 |
| JP | 2005-154402 A | 6/2005 |
| JP | 2005-157702 A | 6/2005 |
| JP | 2005-522495 A | 7/2005 |
| JP | 2006-528506 A | 12/2006 |
| JP | 2007-091710 A | 4/2007 |
| JP | 2008-115129 A | 5/2008 |
| JP | 2008-117969 A | 5/2008 |
| JP | 2009-173631 A | 8/2009 |
| WO | WO-94/13300 A1 | 6/1994 |
| WO | WO-94-16683 A1 | 8/1994 |
| WO | WO-96/040148 A1 | 12/1996 |
| WO | WO-96-40149 A1 | 12/1996 |
| WO | WO-99/34779 A1 | 7/1999 |
| WO | WO-99/64004 A1 | 12/1999 |
| WO | WO-01/00702 A1 | 1/2001 |
| WO | WO-2002-44187 | 6/2002 |
| WO | WO-02/071054 A1 | 9/2002 |
| WO | WO-03/035078 A1 | 5/2003 |
| WO | WO-03/086563 A2 | 10/2003 |
| WO | WO-2003-86563 | 10/2003 |
| WO | WO-2005/011810 A1 | 2/2005 |
| WO | WO-2005-0011810 A1 | 2/2005 |
| WO | WO-2006/133354 A2 | 12/2006 |
| WO | WO-2007-026725 A2 | 3/2007 |
| WO | WO-2008/001851 | 1/2008 |

OTHER PUBLICATIONS

Alexiou et al., "Magnetic mitoxantrone nanoparticle detection by histology, X-ray and MRI after magnetic tumor targeting", Journal of Magnetism and Magnetic Materials, 2001, 225:187-193.

Bhat et al., "Structures and Sterochemistry of New Labdane Diterpenoids from Coleus Forskohlii Briq.", Tetrahedron Letters, 1977, 19:1669-1672.

Fortin-Ripoche et al., "Magnetic Targeting of Magnetoliposomes to Solid Tumors with MR Imaging Monitoring in Mice: Feasibility", Radiology, May 2006, 239(2):415-424.

Gupta, A.K., et al., "Receptor-Mediated Targeting of Magnetic Nanoparticles Using Insulin as a Surface Ligand to Prevent Endocytosis", IEEE Transactions on Nanobioscience, Dec. 2003, 2(4):255-261.

Gupta, P.K., et al., "Magnetically Controlled Targeted Micro-Carrier Systems", Life Sciences, 1989, 44(3):175-186.

Hafeli, et al., "Effective Targeting of Magnetic Radioactive Y-microspheres to Tumor Cells by an Externally Applied Magnetic Field. Preliminary In Vitro and In Vivo Results", Nucl. Med. Biol., 1995, 22(2):147-155.

Kortus, J., "Electronic structure, magnetic ordering and phonons in molecules and solids", Habilitation thesis, Technische Universitat Freiberg, Germany, Dec. 9, 2003, 130 pages.

LeClaire et al., "A Simple Access to a Forskolin Precursor", Tetrahedron Letters, 1989, 30(46):6331-6334.

Leopold et al., "Carcinogenicity of Antitumor cis-Platinum(II) Coordination Complexes in the Mouse and Rat", Cancer Research, Mar. 1979, 39:913-918.

Rotella et al., "N-3-Substituted Imidazoquinazolinones: Potent and Selective PDE5 Inhibitors as Potential Agents for Treatment of Erectile Dysfunction", J. Med. Chem., Apr. 6, 2000, 43(7):1257-1263.

Rotella et al., "Optimization of Substituted N-3-Benzylimidazoquinazolinone Sulfonamides as Potent and Selective PDE5 Inhibitors", J. Med. Chem., Dec. 28, 2000, 43(26):5037-5043.

Sestier et al., "Surface modification of superparamagnetic nanaoparticles (Ferrofluid) studies with particle electrophoresis: Application to the specific targeting of cells", Electrophoresis, 1998, 19:1220-1226.

Srihari et al., "Reactions of Fluorenylidene Nitrile Ylides with (Salen)metal Complexes", Inorg. Chem., 1990, 29:3154-3157.

Takahashi et al., "Heat enhances the cytotoxicity of cis-diamminedichloroplatinum(II) and its analogues cis-1,1-cyclobutanedicarboxylato(2R)-2-methyl-1,4-butanediammineplatinum(II) and cis-diammine(glycolato)platinum in vitro", Cancer Chemother Pharmacol, 1993, 33:31-35.

Torchilin et al., "Magnetic Sephadex as a carrier for enzyme immobilization and drug targeting", Journal of Biomedical Materials Research, 1985, 19:461-466.

Zhang et al., "Surface modification of superparamagnetic magnetite nanoparticles and their intracellular uptake", Biomaterials, 2002, 23:1553-1561.

Lewis et al (Journal of the Chemical Society [Section] A: Inorganic, Physical, & Theoretical, 1967, No. 7, pp. 1014-1 018).

Routier et al (Nucleic Acids Research, 1999, vol. 27, No. 21, pp. 4160-4166).

Routier et al., "DNA cleavage by hydroxy-salicylidene-ethylendiamine-iron complexes," Nucleic Acids Research, vol. 27, No. 21, pp. 4160-4166, 1999.

Fanning et al, "Solid-State and Solution Properties of (N, N-Ethylenebis (salicylideneaminato))(nitro) iron (III) and Related Complexes," Inorganic Chemistry, vol. 24, No. 19, pp. 2884-2889, 1985.

Chinese Office Action dated Dec. 9, 2013 in corresponding Chinese Patent Application No. 200980146570.9.

Chinese Office Action dated Apr. 27, 2013 in corresponding Chinese Patent Application No. 200980146570.9.

Russian Office Action dated Jun. 27, 2012 in corresponding Russian Patent Application No. 2011124913 (7 pages) with an English Translation (4 pages).

Extended European Search Report dated Jun. 4, 2012 in corresponding in European Patent Application No. 09827243.8.

Qi et al., "anti-Spin-Delocalization Effect in Co-C Bond Dissociation Enthalpies." Organometallics, vol. 27, No. 12, pp. 2688-2698, 2008.

Venkataramanan et al., "Electronic and Steric Effects on the Oxygenation of Organic Sulfides and Au Sulfoxides with Oxo(salen)chromium(V) Complexes," Journal of Organic Chemistry, vol. 68, pp. 7460-7470, 2003.

(56) References Cited

OTHER PUBLICATIONS

International Search Report dated Feb. 9, 2010 issued in corresponding International Patent Application No. PCT/182009/007525 (5 pages) with an English Translation (4 pages).
International Search Report dated Sep. 11, 2007 issued in corresponding International Patent Application No. PCT/JP2007/063011 (5 pages) with an English Translation (7 pages).
European Search Report dated Jun. 23, 2008 issued in corresponding European Patent Application No. 06783129.7.
European Search Report dated Nov. 4, 2008 issued in corresponding European Patent Application No. 06783129.7.
European Search Report dated Jun. 9, 2010 issued in corresponding European Patent Application No. 06783129.7.
European Search Report dated Jun. 16, 2009 issued in corresponding European Patent Application No. 07767804.3.
Lewis et al., "The Preparation and Magnetic Properties of Some Oxy-bridged Binuclear Iron (III) Schiff-base Complexes," Journal of the Chemical Society, (A), pp. 1014-1016, 1967.

* cited by examiner

*p<0.05
**p<0.01

IRON-SALEN COMPLEX

CROSS REFERENCE TO RELATED APPLICATIONS

This application is a continuation of U.S. application Ser. No. 12/146,624, filed Jun. 26, 2008, which claims the benefit of Japanese Patent Application No. 2007-338928, filed Dec. 28, 2007, each of which is expressly incorporated by reference herein.

SEQUENCE LISTING

The instant application contains a Sequence Listing which has been submitted in ASCII format via EFS-Web and is hereby incorporated by reference in its entirety. Said ASCII copy, created on Mar. 7, 2016 is named 203106_537410_SL_ST25.txt and is 727 bytes in size.

BACKGROUND

The present invention relates to iron-salen complexes.

RNAi (RNA interference) is a phenomenon in which double-stranded RNA (dsRNA) is taken up into various organisms or cells, resulting in the destruction of complementary mRNA. Long (generally 200 base pair or more) dsRNA is cut up into shorter 21 to 25 base pair siRNA (short interfering RNA) by Dicer, a type of ribonuclease in cells. The double-stranded siRNA is unwound into single strands by helicase in the cytoplasm, resulting in the formation of RISC (RNA-induced silencing complexes) primarily by antisense strands and some proteins. The interaction between the siRNA antisense strands and mRNA results in binding to complementary transcripts, and the ribonuclease activity of the RISC thereby results in the destruction of mRNA and thus gene silencing (the suppression of gene expression).

Because long dsRNA cannot be introduced without modification into mammalian cells, 21 bp chemically synthesized double-stranded siRNA is used. Synthetic double-stranded siRNA has been exploited for gene functional analysis and the screening of target genes because there is no need for the preparations and time required to prepare knock out mice with homologous recombinants, and knock down can be readily brought about by the targeted mRNA degradation using cultured cells or animal models.

The above compounds would be administered to the living body to reach the affected site and bring about pharmacological effects in the local affected site, leading to therapeutic efficacy, but without reaching and treating unaffected tissue (that is, normal tissue). How to effectively guide the drug to the affected site is thus critical in terms of treatment strategy. Techniques for thus guiding the drug to the affected site are referred to as drug delivery, and have become the subject of much recent research and development. This drug delivery has at least two advantages. One is that a sufficiently high concentration of the drug is obtained in the affected tissue. Pharmacological effects will not show up unless the drug concentration is at a certain level in the affected area, and no therapeutic effects can be anticipated at lower concentrations. The second is that the drug is guided only to the affected tissue and not unnecessarily to normal tissue. This can suppress adverse drug reactions.

The most effective drug delivery of this type is cancer treatment with anti-tumor agents. As most anti-tumor agents inhibit the growth of cancer cells that activate mitosis, they also end up inhibiting cell growth in normal mitosis-activating tissue, such as bone marrow, hair roots, and gastrointestinal mucosa. Patients given anti-tumor agents thus suffer from adverse drug reactions such as anemia, hair loss, and vomiting. As such adverse drug reactions impose a major burden on patients, a problem is that doses must be limited, preventing the pharmacological effects of the anti-tumor agents from being fully exploited. Additionally, in the worst cases, patients are at risk of dying from the adverse drug reactions. There is thus a need to be able to achieve effective therapy while suppressing adverse drug reactions by guiding anti-tumor agents to cancer cells by means of drug delivery to allow the agents to be concentrated in cancer tissues and bring about the intended pharmacological effects.

Applications to the treatment of erectile dysfunction, for example, may also be contemplated in addition to anti-tumor agents. There are cases in which drugs for the treatment of erectile dysfunction have interacted with nitrates, leading to serious systemic hypotension and death, a problem which occurs particularly in middle-aged or older men with heart disease. That is because drugs for the treatment of erectile dysfunction are not necessarily limited to the affected area, and affect the systemic vasculature, increasing the vasodilating action of nitrates. Drug delivery may therefore also allow drugs for the treatment of erectile dysfunction to be guided to and concentrated in the affected area to bring about the intended pharmacological effect, thereby suppressing adverse drug reactions resulting from interactions with nitrates.

Delivery to affected tissue using carriers has been studied as a specific method of drug delivery, but this involves loading the drug on a carrier that is readily concentrated in the affected area to transport the drug on the carrier to the affected area. The use of various types of antibodies, microspheres, or magnetic substances as carriers has been studied. Out of these, magnetic substances have been considered useful, and methods for allowing a carrier which is a magnetic substance to adhere to drugs to allow the drug to be concentrated in the affected area by a magnetic field have been studied (such as Japanese Laid-Open Patent Application No. 2001-10978). This method is considered an especially effective method for highly cytotoxic anti-tumor agents because the delivery method is convenient and affected areas can be targeted.

However, it is difficult to make practical use of magnetic substances as carriers in the manner described above because, as noted previously, they are difficult to administer orally, the carrier molecules are generally extremely large, and technical problems have been pointed out with the binding strength to, and affinity for, drug molecules.

SUMMARY

In view of the foregoing, an object of the invention is to provide a drug delivery system that would be easy to use for practical purposes and that would allow conventional technical drawbacks to be overcome.

The present invention provides iron-salen complexes represented by any of the following Formulas (I) to (V).

[C1]

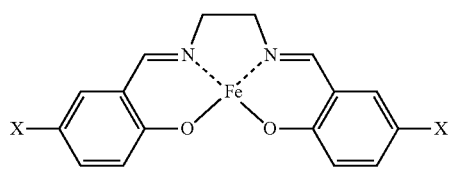
(I)

(where X is any of the following:
—H
—CO₂M$_e$
—CO(OCH₂CH₂)$_n$OCH₃

[C2]

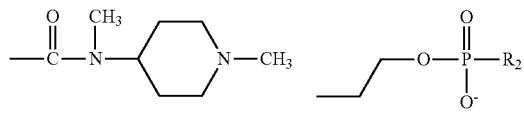

(where R$_2$ comprises a plurality of bound nucleic acids consisting of adenine, guanine, thymine, cytosine, or uracil) or
—NHR$_1$ (where R$_1$ is a substituent with a hydroxyl)

[C3]

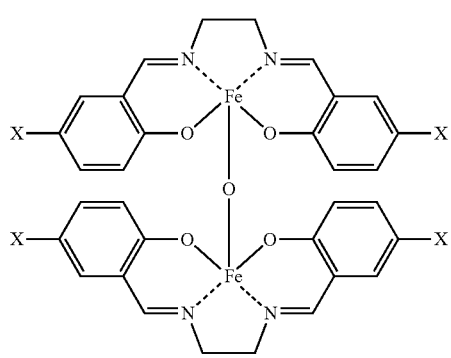
(II)

(where X is —NHR$_1$ (where R$_1$ is a substituent with a hydroxyl), —Cl, —Br, or —H)

[C4]

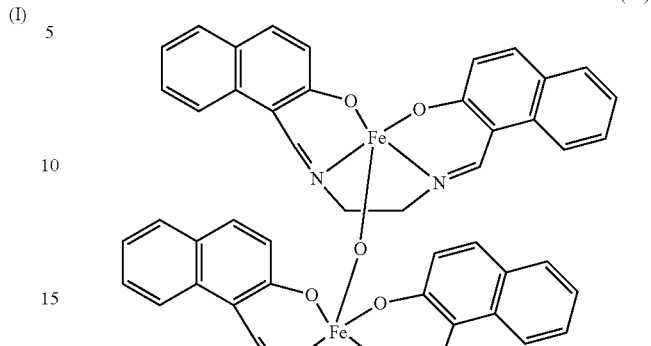
(III)

[C5]

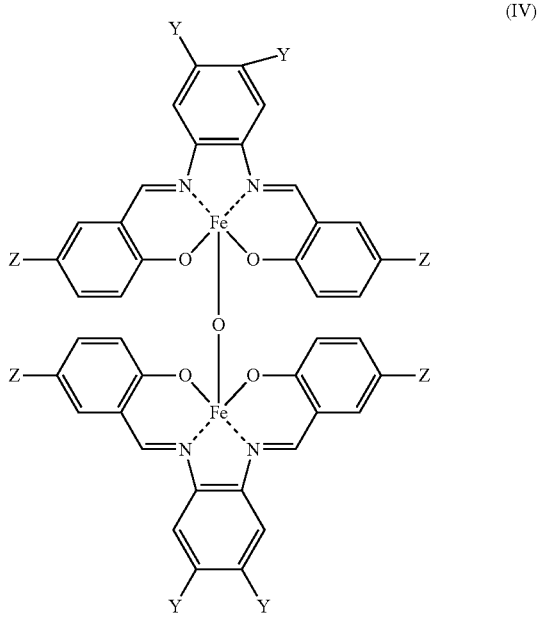
(IV)

(where Y is —H, —NH₂, or —NHR$_1$ (where R$_1$ is a substituent with a hydroxyl), and Z is —Cl or —NHR$_1$ (where R$_1$ is a substituent with a hydroxyl))

[C6]

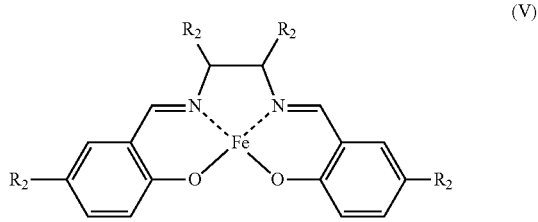
(V)

(where R$_1$ is —Cl or —NHR$_1$ (where R$_1$ is a substituent with a hydroxyl), and R$_2$ is —H, —NH₂, or —NHR$_1$ (where R$_1$ is a substituent with a hydroxyl)).

The iron-salen complexes of the invention have a specific structure represented by the above Formulas (I) to (IV), resulting in better water solubility and magnetic properties.

The binding of substituents with an abundance of hydrogen bonds at both ends results in better water solubility and magnetic properties.

The iron-salen complexes of the invention are magnetic, and can thus provide magnetic drugs binding certain compounds.

The invention renders iron-salen complexes magnetic, which can thus be used as drugs that can be delivered to affected areas in the body using the inherent magnetic properties of the drug without employing carriers composed of magnetic substances as was done in the past.

An AC magnetic field can be applied to the drug to increase the temperature and destroy cancer cells.

It is thus possible to provide a drug delivery system that is easy to use for practical purposes and that overcomes the above conventional problems of difficult oral administration, extremely large carrier molecules, and technical problems with the binding strength to, and affinity for, drug molecules.

DETAILED DESCRIPTION

Figure 1:
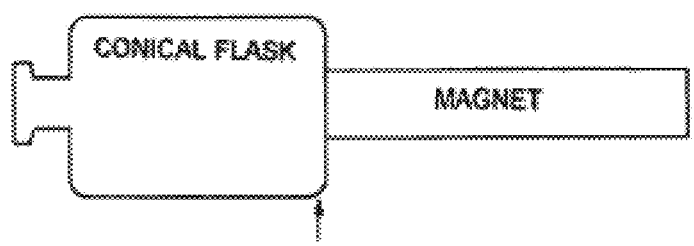
FIG. 1 is a block diagram schematically illustrating a test system for demonstrating the whereabouts of the drug in a magnetic field.

Embodiments of the invention are described below. The following embodiments are intended to illustrate the invention, and are not intended to limit the invention to these embodiments alone. The invention is capable of a variety of embodiments without departing from the spirit of the invention.

Iron-Salen Complexes

The iron-salen complexes of the invention are represented by any of the following Formulas (I) to (V).

[C1]

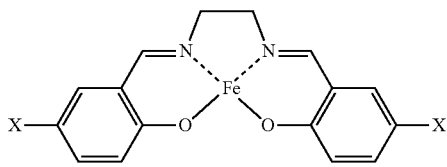

(I)

(where X is any of the following:
—H
—$CO_2M_e$
—$CO(OCH_2CH_2)_nOCH_3$

[C2]

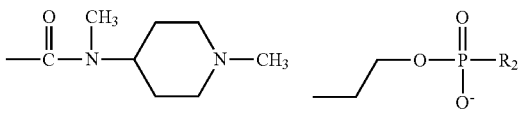

(where $R_2$ comprises a plurality of bound nucleic acids consisting of adenine, guanine, thymine, cytosine, or uracil) or —$NHR_1$ (where $R_1$ is a substituent with a hydroxyl)

[C3]

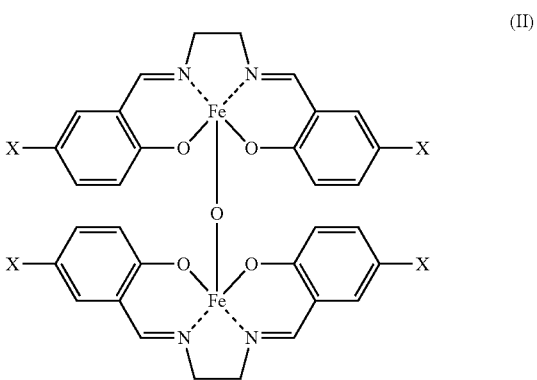

(II)

(where X is —$NHR_1$ (where $R_1$ is a substituent with a hydroxyl), —Cl, —Br, or —H)

[C4]

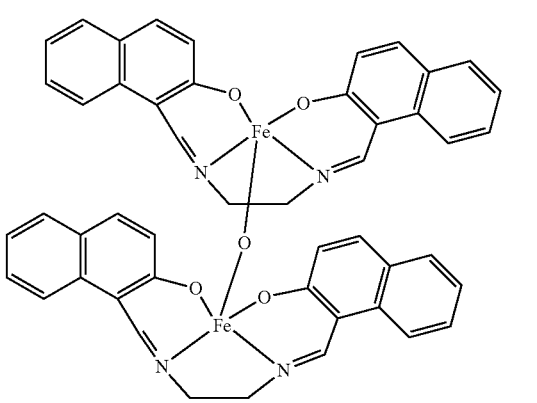

(III)

[C5]

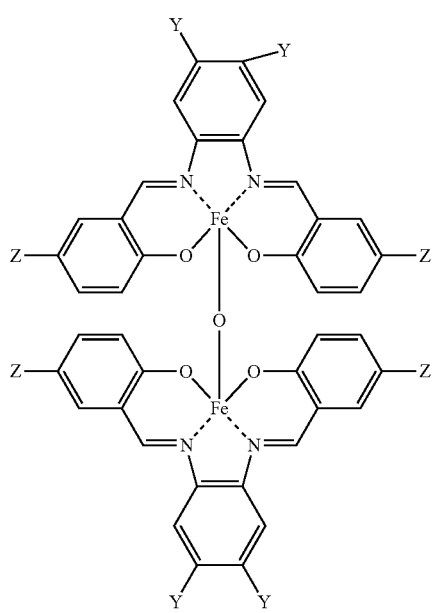

(IV)

(where Y is —H, —NH$_2$, or —NHR$_1$ (where R$_1$ is a substituent with a hydroxyl), and Z is —Cl or —NHR$_1$ (where R$_1$ is a substituent with a hydroxyl))

[C6]

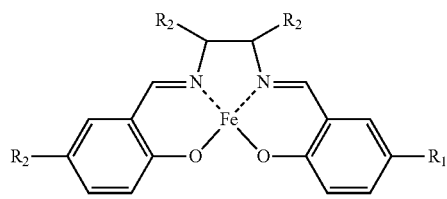

(V)

(where R$_1$ is —Cl or —NHR$_1$ (where R$_1$ is a substituent with a hydroxyl), and R$_2$ is —H, —NH$_2$, or —NHR$_1$ (where R$_1$ is a substituent with a hydroxyl)).

The charge transfer of R$_1$ is preferably less than 0.5 electrons (e).

R$_1$ is preferably a substituent which is the result of a hydrogen leaving any of the compounds of the following Formulas (1) to (27).

[C7]

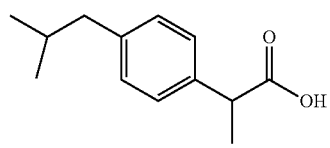

ibuprofen (1): ibuprofen piconol, phenylpropionic acid analgesics/anti-inflammatories

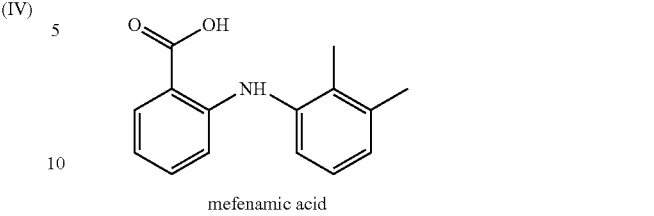

mefenamic acid (2): mefenamic acid, anthranilic acid antipyretic anti-inflammatory analgesics

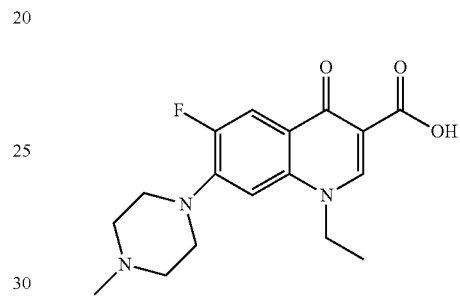

pefloxacin (3) drugs for treating hyperlipemia

[C8]

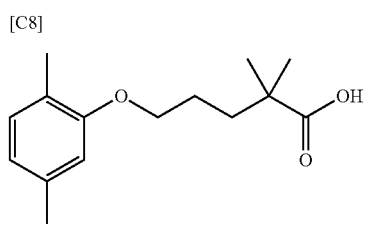

gemfibrozil (4): antibacterials

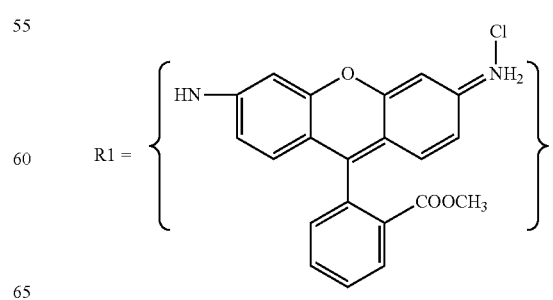

R1 =

(5): fluorochromes (rhodamines)
[C9]
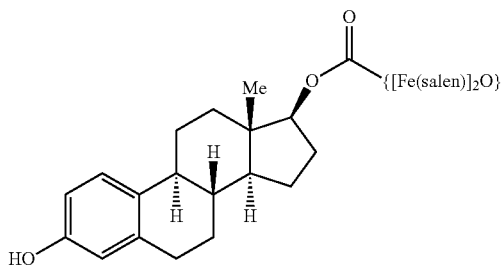
(6): hormones (estrogen)
[C10]
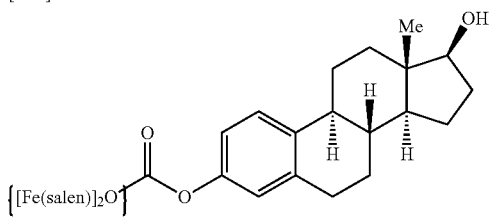
(7): hormones (estrogen)
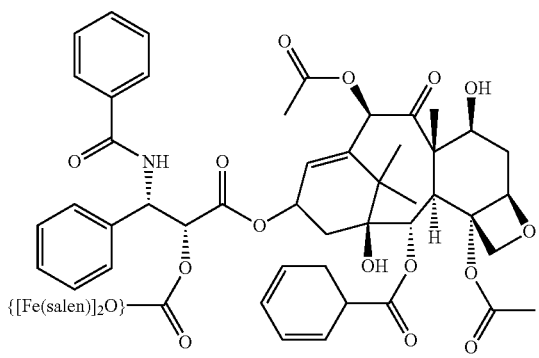
(8): Taxol (paclitaxel)
[C11]
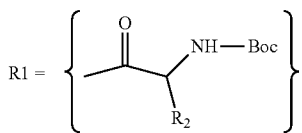
(9): amino acids (glycine)
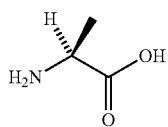
(10): amino acids (alanine)
[C12]
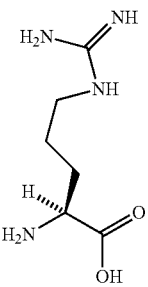
(11): amino acids (arginine)
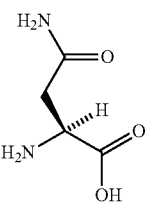
(12): amino acids (asparagine)
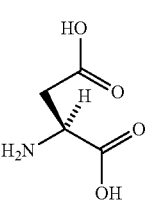
(13): amino acids (aspartic acid)
[C13]
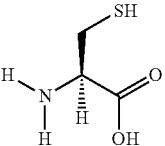
(14) amino acids (cysteine)
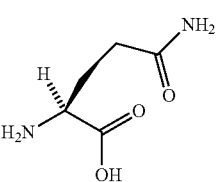

(15): amino acids (glutamic acid)
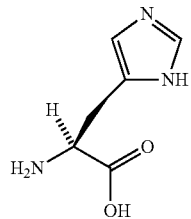 [SMILES: N[C@@H](Cc1cnc[nH]1)C(=O)O]
(16): amino acids (histidine)
[C14]
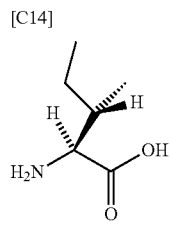
(17): amino acids (isoleucine)
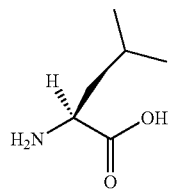
(18): amino acids (leucine)
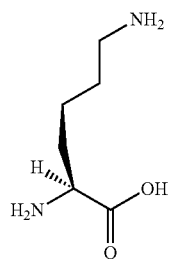
(19): amino acids (lysine)
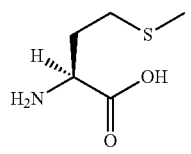
(20): amino acids (methionine)
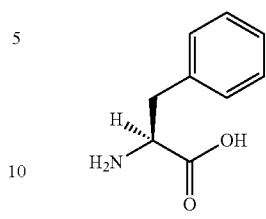
(21): amino acids (phenylalanine)
[C15]
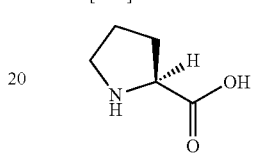
(22): amino acids (proline)
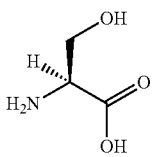
(23): amino acids (serine)
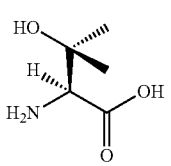
(24): amino acids (threonine)
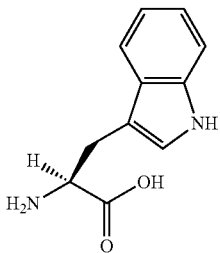 [SMILES: N[C@@H](Cc1c[nH]c2ccccc12)C(=O)O]

(25): amino acids (tryptophan)
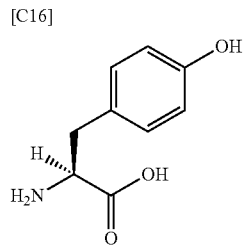
[C16]
(26): amino acids (tyrosine)
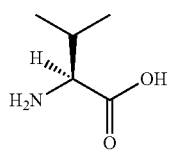
(27): amino acids (valine)
Preferred specific examples of the iron-salen complexes of the invention are given below.
[C18]
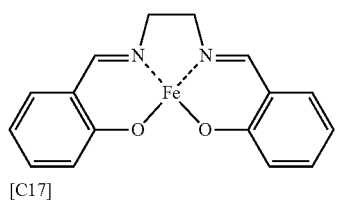
[C17]
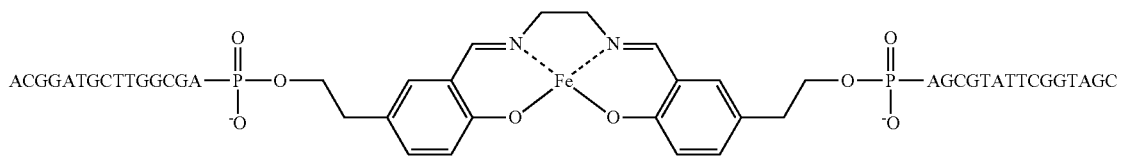
[C19]
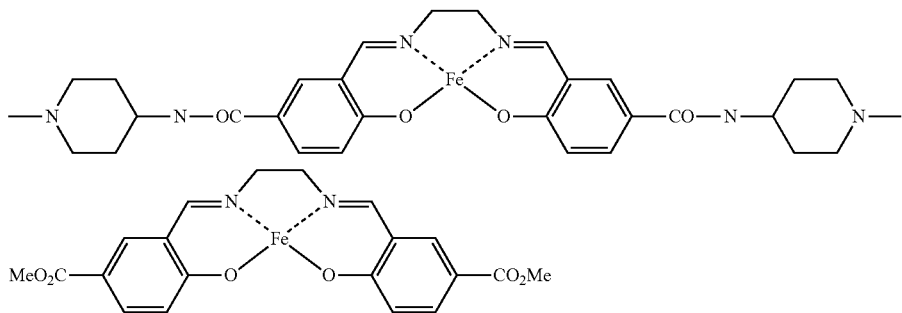
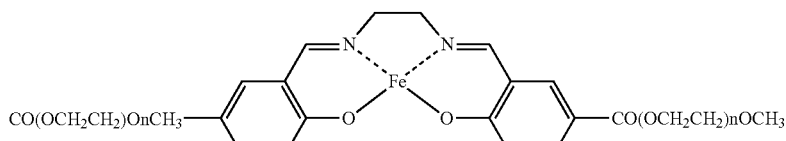
[C20]
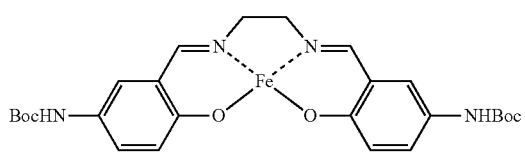

[C21]
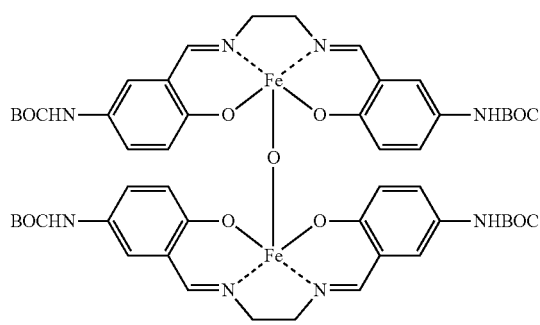
[C22]
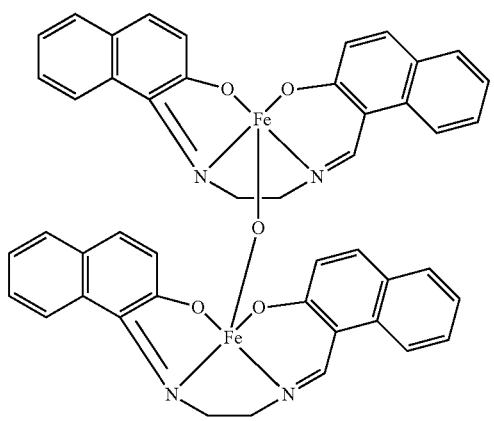
[C23]
-continued
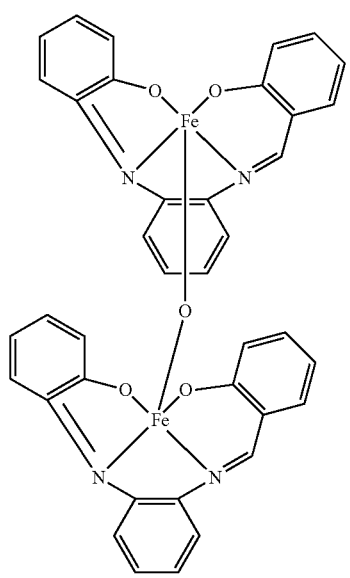
[C24]
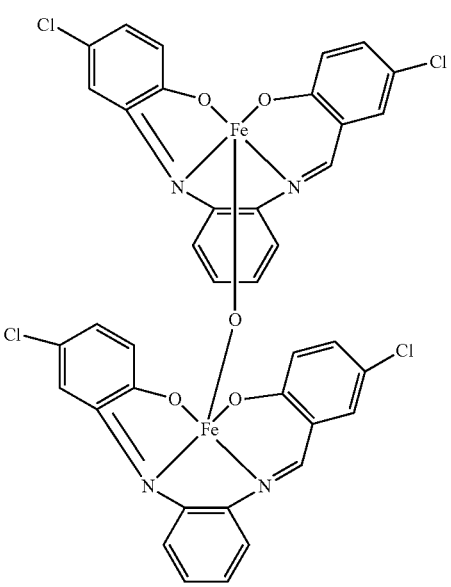

-continued

[Chemical structure: binuclear iron-salen complex with two Fe centers bridged by oxygen, each Fe coordinated by a salen-type ligand]

The above compounds can be synthesized, for example, as noted in J. Lewis, F. E. Mabbs, and A. Richards, "The Preparation and Magnetic Properties of Some Oxy-bridged Binuclear Iron (III) Schiff-base Complexes," *J. Chem. Soc.* (A), 1014-1018 (1968).

(Drugs)

The drugs of the invention are composed of the above iron-salen complexes.

In one example of the use of a drug in the invention, after the inherently magnetic drug has been administered to an individual, a magnetic filed can be applied to the individual to guide the drug to the target tissue or affected area.

In another example of use, means for generating magnetism in the tissue or affected site of the individual can be employed to guide the drug to the tissue or affected site.

In yet another example of use, means for generating magnetism can be disposed in a pathway such as a blood vessel supplying the bodily fluids of the individual to the tissue or affected site of the individual, so as to guide the drug to the tissue or affected site downstream.

In still another example of use, a drug composed of an iron-salen complex in which R1 is rhodamine (fluorophore) is irradiated so as to emit light, which is detected to sense the pharmacokinetics of the drug.

In another example of use, after the drug has been guided by a magnetic field to the affected site, an AC magnetic filed can be applied to the drug, increasing the temperature around the cancer cells to a temperature resulting in the destruction of the cancer cells and destroying only the cancer cells.

(Drug Delivery System)

The drugs of the invention can be used in drug delivery systems by which drugs administered into the body are guided by the magnetism of the drugs to a target affected area, where means are disposed for generating a magnetic field at the surface, tissue, or affected site of the individual.

The drugs of the invention can also be used in drug delivery systems by which drugs administered into the body are guided by the magnetism of the drugs to a target affected site, where the system is equipped with means for generating a magnetic field in the individual and means for guiding the magnetic field to the target tissue or affected site of the individual.

The means for generating the magnetic field is preferably designed so that the target tissue or affected site is located between a pair of magnets, allowing flux to be concentrated in the tissue or affected site.

(Magnetic Sensors)

The target tissue or affected site is preferably identified by MRI or CT.

The drugs of the invention can be used in magnetic sensors, where the magnetism or light emission of drugs administered into the body is detected to sense the pharmacokinetics of the drug.

The magnetism of the drugs is preferably detected by magnetic resonance induction or light emission.

(Functional Diagnosis, Chemotherapy, Biothermia)

In another example of the use of the drugs of the invention, an electromagnetic field can be applied to the drug which has been introduced into cancer tissue so as to locally elevate the temperature and selectively destroy the cancer cells.

The use of the iron-salen complexes of the invention will allow one drug to be used in functional diagnosis, MRI diagnostic devices, chemotherapy, biothermia, and magnetic induction drug delivery systems.

(Drug Design)

In another example of the use of the drugs of the invention, molecular models of drugs can be established, it can be determined whether the molecular models are magnetic based on the mathematically calculated spin charge density for the molecular models, and drugs can be designed based on molecular models that have been determined to be magnetic.

This method for designing drugs allows drugs to be designed by mathematical calculations such that the exchange of electrons in compounds ($R_1$) bound at both ends is less than 0.5 electrons (e).

This method for designing drugs allows the magnetic intensity of molecular models to be determined based on the spin charge density distribution.

EXAMPLES

The invention is illustrated in further detail by, but is not limited to, the following examples.

Example 1

An iron-salen complex was synthesized in the following manner.

Step 1:

[C25]

[Chemical reaction scheme: 4-nitrophenol ($C_6H_5NO_3$, Mol. Wt.: 139.11, 25 g, compound 1) reacted with HMTA in PPA at 100° C. with 57% yield to give 2-formyl-4-nitrophenol ($C_7H_5NO_4$, Mol. Wt.: 167.12, 17 g, compound 2)]

A mixture of 4-nitrophenol (25 g, 0.18 mol), hexamethylene tetramine (25 g, 0.18 mol), and polyphosphoric acid (200 mL) was stirred for 1 hour at 100° C. The mixture was then introduced into 500 mL of ethyl acetate and 1 L of water, and was stirred until completely dissolved. When 400 mL of ethyl acetate was further added to the solution, the solution separated into two phases, the aqueous phase was removed, and the remaining compound was washed twice with basic solvent and dried over anhydrous MgSO4, allowing 17 g of Compound 2 to be synthesized (57% yield).

Step 2:

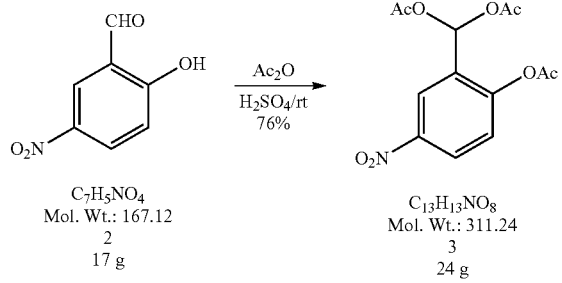

Compound 2 (17 g, 0.10 mol), acetic anhydride (200 mL), and H₂SO₄ (minimal) were stirred for 1 hour at room temperature. The resulting solution was mixed for 0.5 hour in iced water (2 L) to bring about hydrolysis. The resulting solution was filtered and dried in air, giving a white powder. The powder was recrystallized from solvent containing ethyl acetate, giving 24 g of Compound 3 (76% yield) in the form of white crystals.

Step 3:

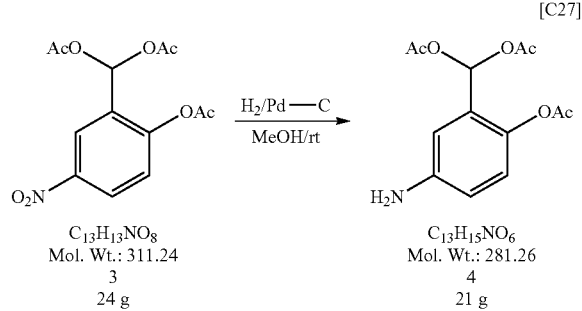

A mixture of carbon (2.4 g) supporting 10% palladium with Compound 3 (24 g, 77 mmol) and methanol (500 mL) was reduced over night in a 1.5 atm hydrogen reducing atmosphere. After completion, the product was filtered, allowing Compound 4 (21 g) in the form of a brown oil to be synthesized.

Step 4, 5:

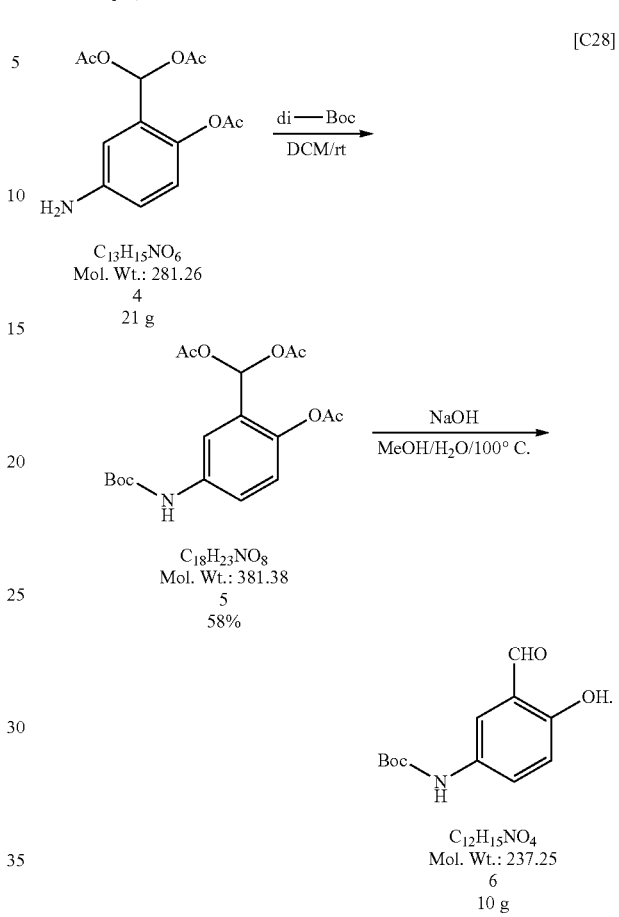

Compound 4 (21 g, 75 mmol) and di(tert-butyl) dicarbonate (18 g, 82 mmol) were stirred over night in anhydrous dichloromethane (DCM) (200 mL) in a nitrogen atmosphere. The resulting solution was allowed to evaporate in a vacuum and then dissolved in methanol (100 mL). Sodium hydroxide (15 g, 374 mmol) and water (50 mL) were then added, and the solution was brought to reflux for 5 hours. The solution was then cooled, filtered, washed with water, and allowed to dry in a vacuum, giving a brown compound.

The resulting compound was processed twice by flash chromatography using silica gel, giving 10 g of Compound 6 (58% yield).

Step 6:

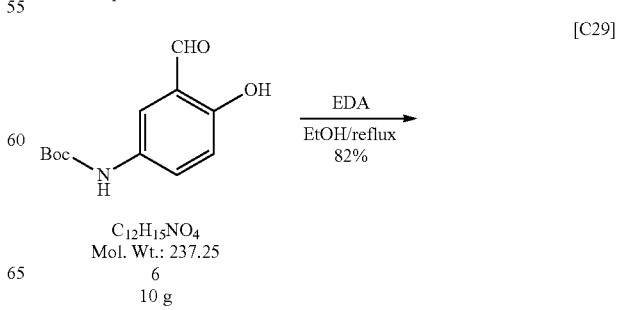

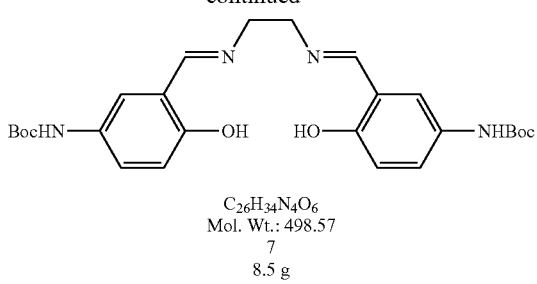

C$_{26}$H$_{34}$N$_4$O$_6$
Mol. Wt.: 498.57
7
8.5 g

Compound 6 (10 g, 42 mmol) was introduced into 400 mL of anhydrous ethanol, the mixture was brought to reflux while heated, and several drops of ethylene diamine (1.3 g, 21 mmol) were added while stirred for 0.5 hour into 20 mL anhydrous ethanol. The mixture was introduced into a container of ice, where it was cooled and mixed for 15 minutes. It was then washed with 200 mL ethanol, filtered, and dried in a vacuum, giving 8.5 g (82% yield) of Compound 7.

Step 7:

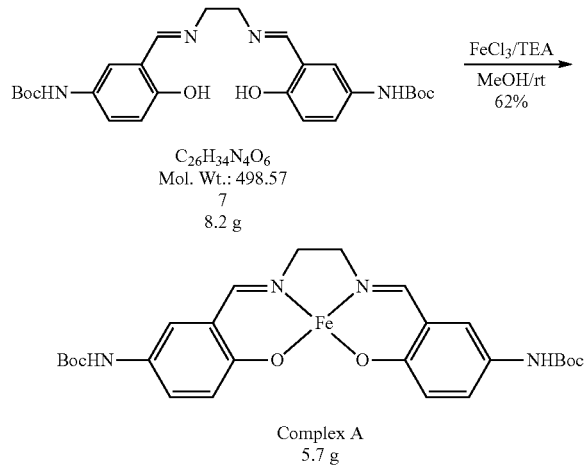

[C30]

Compound 7 (8.2 g, 16 mmol) and triethylamine (22 mL, 160 mmol) were introduced into anhydrous methanol (50 mL), and a solution of FeCl$_3$ (2.7 g, 16 mmol) added to 10 mL methanol was mixed in a nitrogen atmosphere. The ingredients were mixed for 1 hour in a nitrogen atmosphere at room temperature, giving a brown compound. The compound was then dried in a vacuum. The resulting compound was diluted with 400 mL dichloromethane, washed twice with basic solution, and dried in a vacuum, giving Complex A.

The resulting compound was recrystallized from a solution of paraffin and diethyl ether, and assay by HPLC revealed 5.7 g (62% yield) of Complex A (iron-salen complex) with a purity of at least 95%.

—NHR$_1$, substituents —CO$_2$Me with an abundance of hydrogen bonds, —CO(OCH$_2$CH$_2$)nOCH$_3$, or

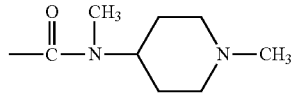

[C31]

were bonded to both ends through acylation and a reaction step with Et3N, etc.

Example 2

An iron-salen complex was synthesized in the following manner.

Step 1:

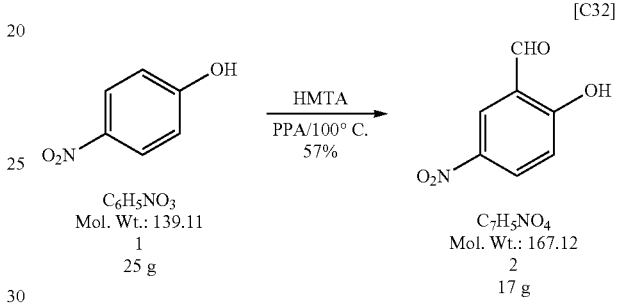

[C32]

A mixture of 4-nitrophenol (25 g, 0.18 mol), hexamethylene tetramine (25 g, 0.18 mol), and polyphosphoric acid (200 mL) was stirred for 1 hour at 100° C. The mixture was then introduced into 500 mL of ethyl acetate and 1 L of water, and was stirred until completely dissolved. When 400 mL of ethyl acetate was further added to the solution, the solution separated into two phases, the aqueous phase was removed, and the remaining compound was washed twice with basic solvent and dried over anhydrous MgSO4, allowing 17 g of Compound 2 to be synthesized (57% yield).

Step 2:

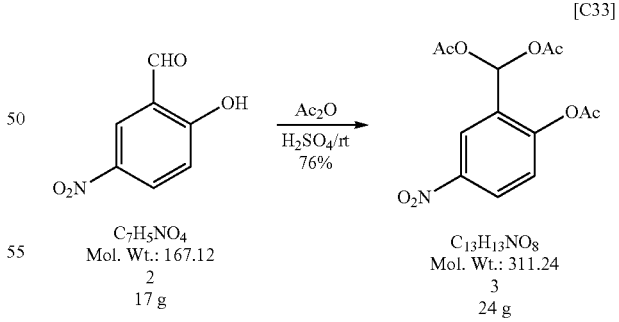

[C33]

Compound 2 (17 g, 0.10 mol), acetic anhydride (200 mL), and H$_2$SO$_4$ (minimal) were stirred for 1 hour at room temperature. The resulting solution was mixed for 0.5 hour in iced water (2 L) to bring about hydrolysis. The resulting solution was filtered and dried in air, giving a white powder. The powder was recrystallized from solvent containing ethyl acetate, giving 24 g of Compound 3 (76% yield) in the form of white crystals.

Step 3:

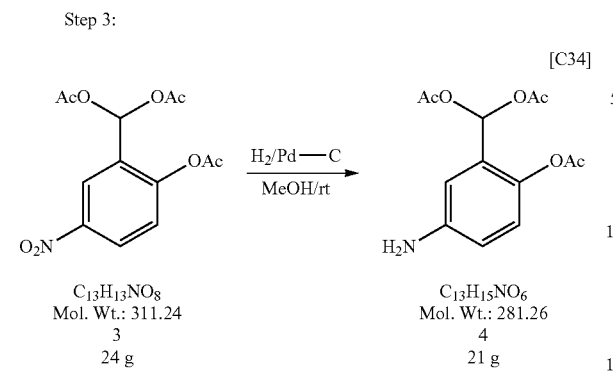
[C34]

C$_{13}$H$_{13}$NO$_8$
Mol. Wt.: 311.24
3
24 g

C$_{13}$H$_{15}$NO$_6$
Mol. Wt.: 281.26
4
21 g

A mixture of carbon (2.4 g) supporting 10% palladium with Compound 3 (24 g, 77 mmol) and methanol (500 mL) was reduced over night in a 1.5 atm hydrogen reducing atmosphere. After completion, the product was filtered, allowing Compound 4 (21 g) in the form of a brown oil to be synthesized.

Step 4, 5:

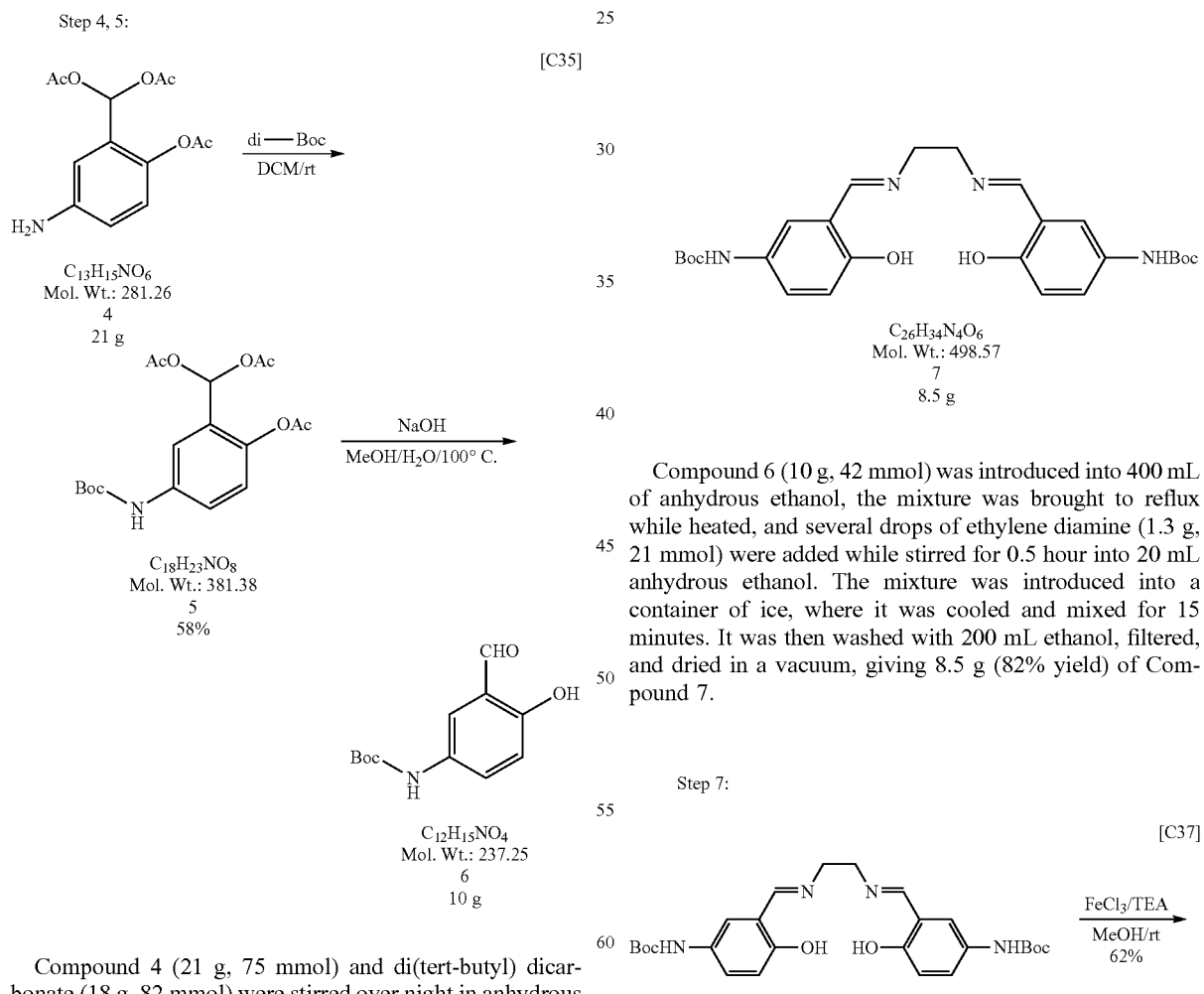
[C35]

C$_{13}$H$_{15}$NO$_6$
Mol. Wt.: 281.26
4
21 g

C$_{18}$H$_{23}$NO$_8$
Mol. Wt.: 381.38
5
58%

C$_{12}$H$_{15}$NO$_4$
Mol. Wt.: 237.25
6
10 g

Compound 4 (21 g, 75 mmol) and di(tert-butyl) dicarbonate (18 g, 82 mmol) were stirred over night in anhydrous dichloromethane (DCM) (200 mL) in a nitrogen atmosphere. The resulting solution was allowed to evaporate in a vacuum and then dissolved in methanol (100 mL). Sodium hydroxide (15 g, 374 mmol) and water (50 mL) were then added, and the solution was brought to reflux for 5 hours. The solution was then cooled, filtered, washed with water, and allowed to dry in a vacuum, giving a brown compound. The resulting compound was processed twice by flash chromatography using silica gel, giving 10 g of Compound 6 (58% yield).

Step 6:

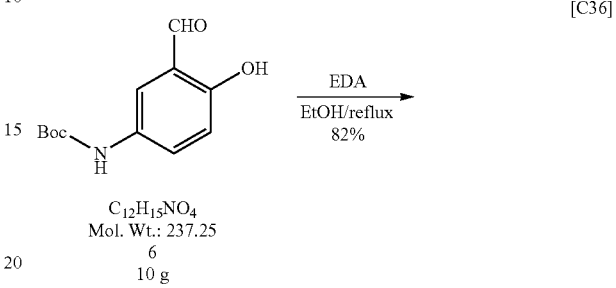
[C36]

C$_{12}$H$_{15}$NO$_4$
Mol. Wt.: 237.25
6
10 g

C$_{26}$H$_{34}$N$_4$O$_6$
Mol. Wt.: 498.57
7
8.5 g

Compound 6 (10 g, 42 mmol) was introduced into 400 mL of anhydrous ethanol, the mixture was brought to reflux while heated, and several drops of ethylene diamine (1.3 g, 21 mmol) were added while stirred for 0.5 hour into 20 mL anhydrous ethanol. The mixture was introduced into a container of ice, where it was cooled and mixed for 15 minutes. It was then washed with 200 mL ethanol, filtered, and dried in a vacuum, giving 8.5 g (82% yield) of Compound 7.

Step 7:

[C37]

BocHN—⟨⟩—OH  HO—⟨⟩—NHBoc
      =N      N=
         \  /

FeCl$_3$/TEA
MeOH/rt
62%

C$_{26}$H$_{34}$N$_4$O$_8$
Mol. Wt.: 498.57
7
8.2 g

25

-continued

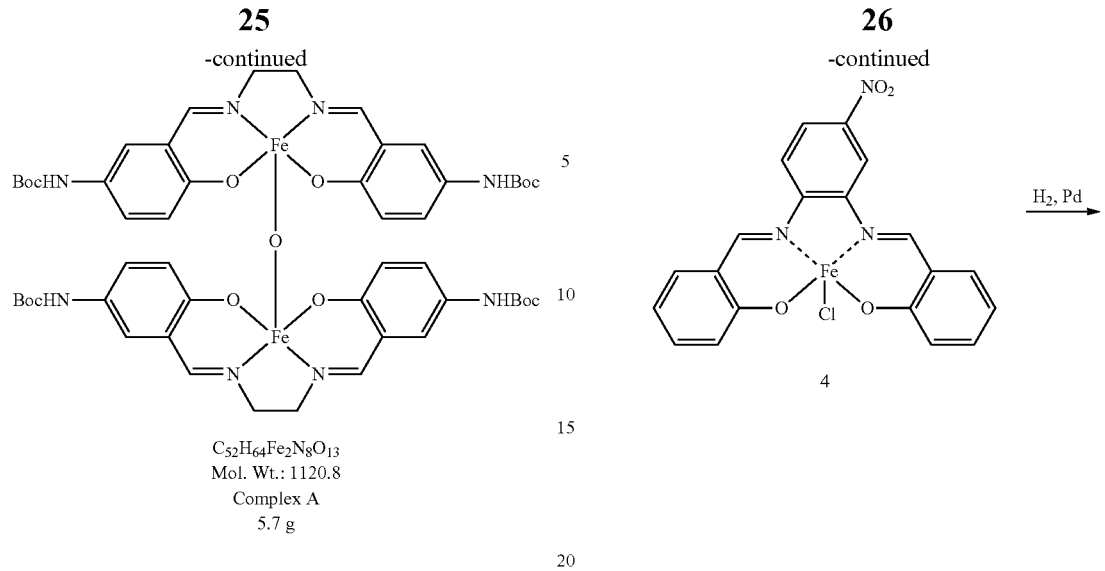

C$_{52}$H$_{64}$Fe$_2$N$_8$O$_{13}$
Mol. Wt.: 1120.8
Complex A
5.7 g

Compound 7 (8.2 g, 16 mmol) and triethylamine (22 mL, 160 mmol) were introduced into anhydrous methanol (50 mL), and a solution of FeCl$_3$ (2.7 g, 16 mmol) added to 10 mL methanol was mixed in a nitrogen atmosphere. The ingredients were mixed for 1 hour in a nitrogen atmosphere at room temperature, giving a brown compound. The compound was then dried in a vacuum. The resulting compound was diluted with 400 mL dichloromethane, washed twice with basic solution, dried with Na2SO4, and dried in a vacuum, giving Complex A. The resulting compound was recrystallized from a solution of paraffin and diethyl ether, and assay by HPLC revealed 5.7 g (62% yield) of Complex A (iron-salen complex) with a purity of at least 95%.

—NHR$_1$ was bonded to both ends through acylation and a reaction step with Et3N, etc.

Example 3

An iron-salen complex was synthesized in the following manner.

26

-continued

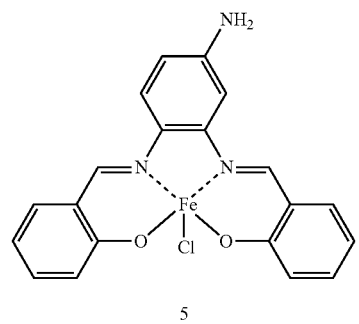

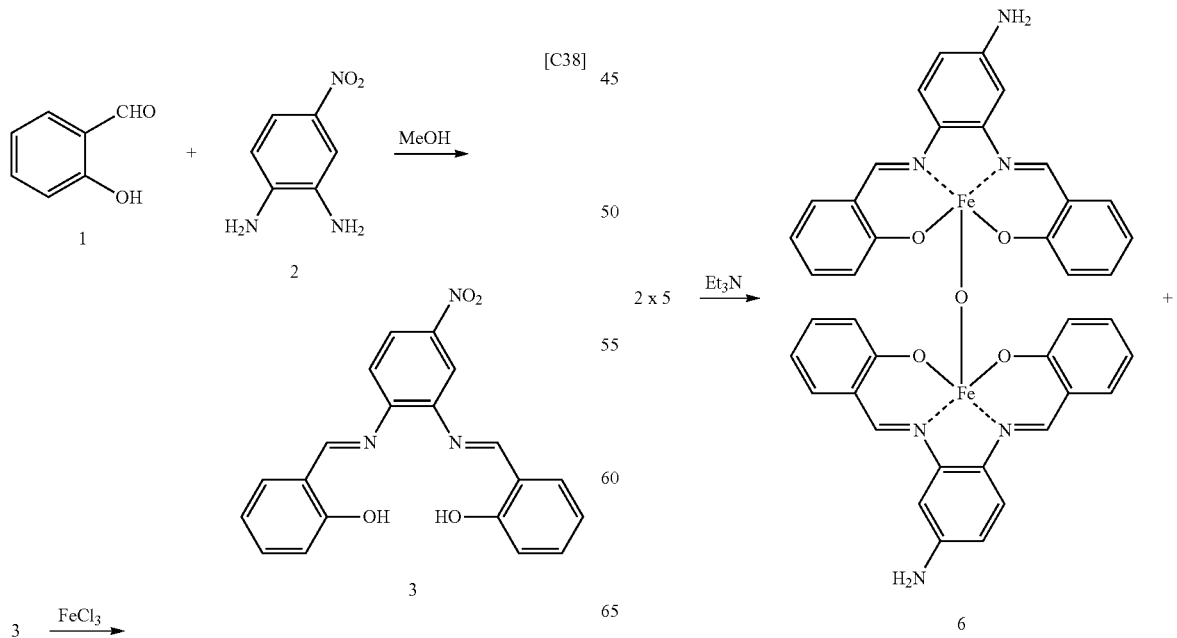

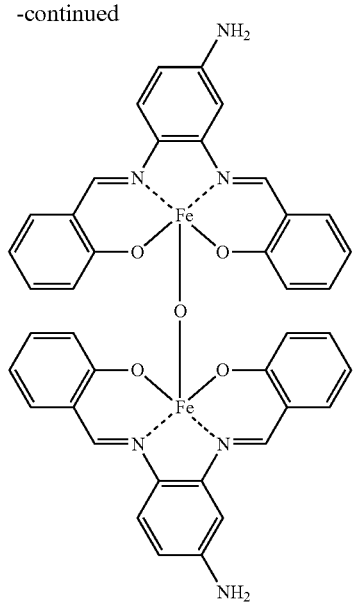

7

A. imine formation
B. iron complex formation
C. reduction
D. μ-oxo-iron complex formation
 —NHR₁ was then bonded to both ends through acylation and a reaction step with Et3N, etc.

Example 4

The electron transfer of the compounds of Formulas (I) to (IV) and the compounds bonded to them can be determined by first principles calculation.

A system for computer simulation was equipped with well-known hardware as the computer, that is, memory, a computing device equipped with computing circuitry such as a CPU, and display means for the output of the computed results. The memory included data specifying existing organic compound or three-dimensional structures, and software programs for performing computer simulation. The software was capable of adding, modifying, and deleting compound side chains, cross linking certain side chains, calculating areas of high spin charge density, and determining the spin charge density for structures as a whole. A commercially available program (Dmol3, by Accelrys) can be used, for example.

The user inputs the position where the side chains are to be added to a compound or selects one in which the side chains are modified or deleted, and uses a memory back up program to designate on the computer the location where cross linking should be formed. The computer receives the input values to calculate the spin charge density, and outputs the results on the display screen. The user can also add structural data on existing compounds to the computer system to obtain the spin charge density of existing compounds.

The charge transfer bonding to iron-salen complexes (Chemical Formula (I)) and the $R_1$ moiety can be determined by integrating the previously determined upward and downward spin charge density in three-dimensional space.

The calculated results for charge transfer are given in Table 1. Table 1 shows the charge transfer binding to iron-salen complexes (Chemical Formula (I)) and to the $R_1$ moiety. A minus sign indicates an increase of electrons. A plus sign indicates a decrease of electrons.

TABLE 1

| Iron-salen complex | Bonded compounds ($R_1$) | |
|---|---|---|
| Formula (I) Charge transfer | Compound name | Charge transfer |
| −0.31 | Ibuprofen Chemical Formula (1) | +0.31 |
| −0.31 | Mefenamic acid Chemical Formula (2) | +0.31 |
| −0.32 | Pefloxacin Chemical Formula (3) | +0.32 |
| −0.31 | Gemfibrozil Chemical Formula (4) | +0.31 |
| −0.32 | Rhodamine Chemical Formula (5) | +0.32 |
| −0.35 | Estrogen Chemical Formula (6) | +0.35 |
| −0.35 | Estrogen Chemical Formula (7) | +0.35 |
| −0.34 | Taxol Chemical Formula (8) | +0.34 |
| −0.28 | Glycine Chemical Formula (9) | +0.28 |
| −0.28 | Alanine Chemical Formula (10) | +0.28 |
| −0.27 | Arginine Chemical Formula (11) | +0.27 |
| −0.27 | Asparagine Chemical Formula (12) | +0.27 |
| −0.25 | Aspartic acid Chemical Formula (13) | +0.25 |
| −0.26 | Cysteine Chemical Formula (14) | +0.26 |
| −0.26 | Glutamic acid Chemical Formula (15) | +0.26 |
| −0.25 | Histidine Chemical Formula (16) | +0.25 |
| −0.27 | Isoleucine Chemical Formula (17) | +0.27 |
| −0.26 | Leucine Chemical Formula (18) | +0.26 |
| −0.24 | Lysine Chemical Formula (19) | +0.24 |
| −0.28 | Methionine Chemical Formula (20) | +0.28 |
| −0.29 | Phenylalanine Chemical Formula (21) | +0.29 |
| −0.26 | Proline Chemical Formula (22) | +0.26 |
| −0.26 | Serine Chemical Formula (23) | +0.26 |
| −0.25 | Threonine Chemical Formula (24) | +0.25 |
| −0.28 | Tryptophan Chemical Formula (25) | +0.28 |
| −0.29 | Tyrosine Chemical Formula (26) | +0.29 |
| −0.25 | Valine Chemical Formula (27) | +0.25 |

Example 5

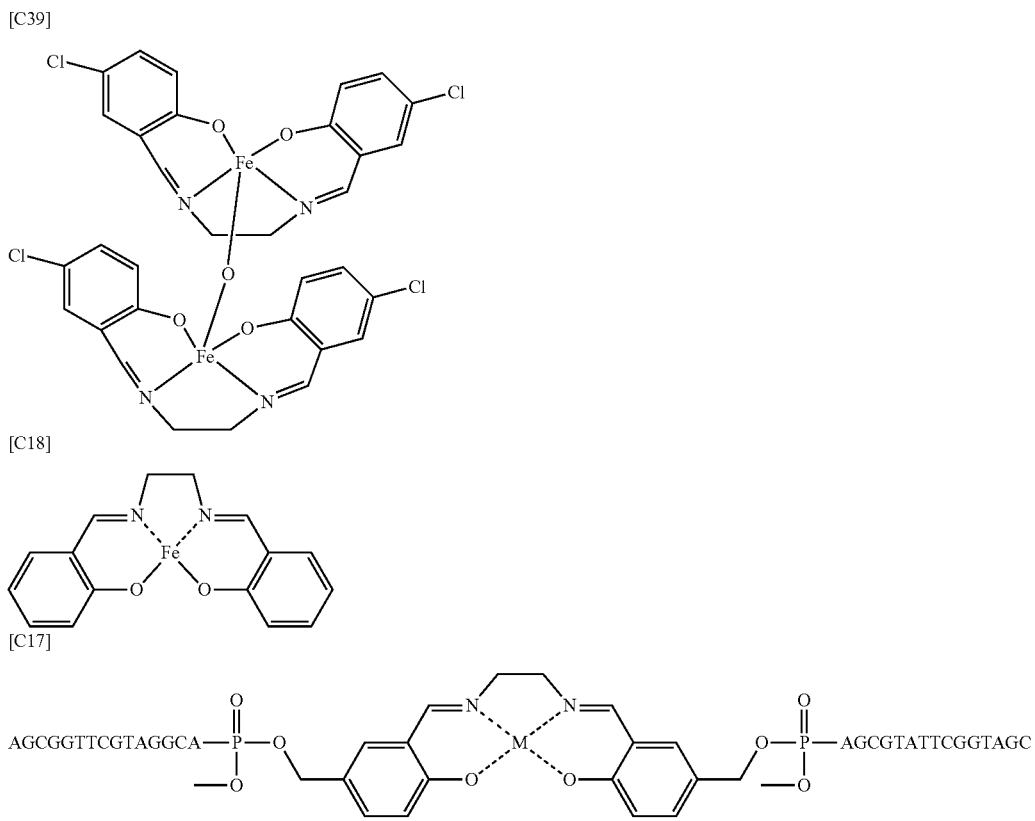

The following experiment was conducted using the various iron-salen complexes represented by the above formulas.

Culture medium was sprinkled with iron-salen complex powder of the above formulas in amounts allowing magnetic attraction to be visibly observed at a rat L6 cell confluence of 30%, and the state of the medium was photographed after 48 hours.

Figure 2:
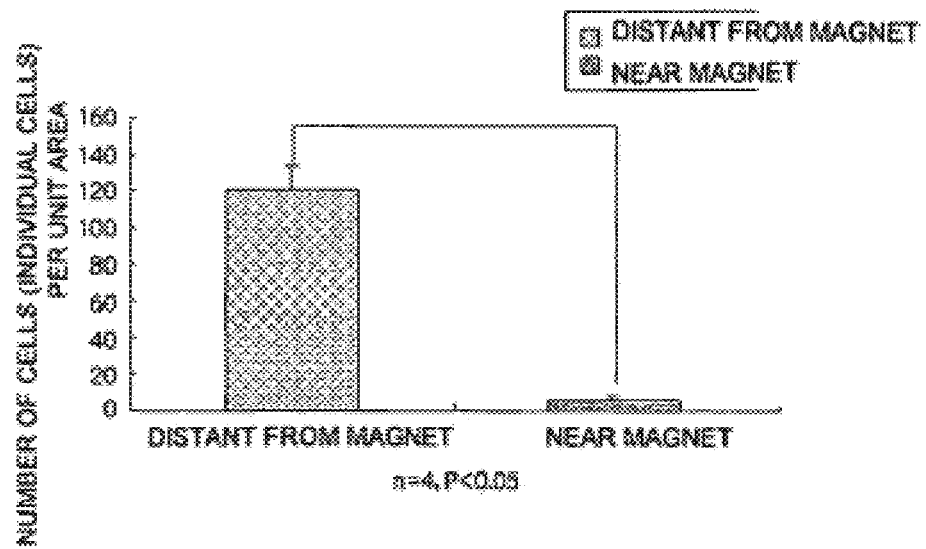
FIG. 2 is a characteristics chart showing the results for cell count based on changes in drug concentration in a magnetic field.

FIG. 1 shows a magnet rod in contact with a conical flask containing rat L6 cell culture medium. After 48 hours, the floor of the conical flask was photographed from one end to the other, and the cell count was calculated, with the results shown in FIG. 2. In FIG. 2, the part near the magnet shows the area of the magnet end surface at the floor of the conical flask, and the part at a distance from the magnet shows the region on the side opposite the magnet end surface at the floor of the conical flask.

FIG. 2 shows that, near the magnet, the iron-salen complexes were attracted, resulting in a greater iron-salen complex concentration, so that the DNA-growth inhibition action of the iron-salen complexes resulted in a dramatically lower number of cells than farther away. A system equipped with magnetism-generating means and drugs rendered magnetic by the present invention can thus allow drugs to become concentrated in target tissues and affected sites of individuals.

Figure 3:
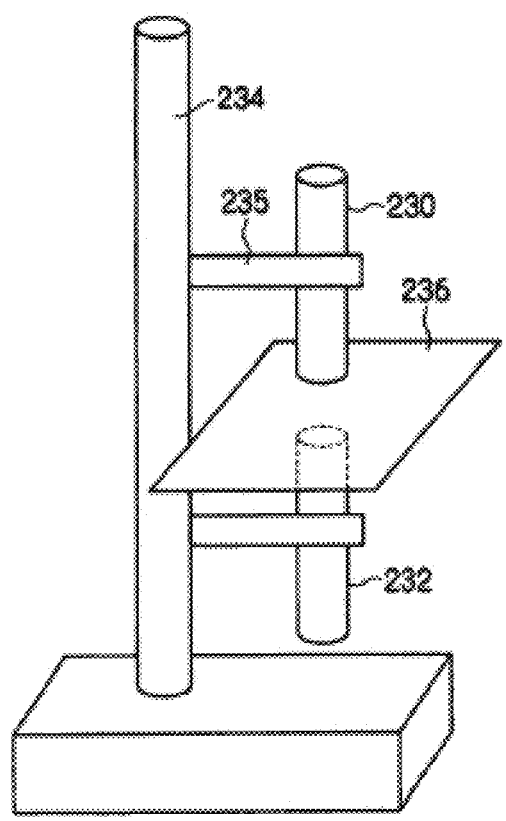
FIG. 3 is a perspective view showing another embodiment of the delivery device of the invention.

Another example of the delivery device of the invention is described next. In this delivery device, as illustrated in FIG. 3, a pair of magnets 230 and 232 facing each other in the direction of gravity are supported by a stand 234 and clamp 235, and a metal plate 236 is located between the magnets. The metal plate, especially an iron plate, is placed between the pair of magnets to locally create a magnetic field of uniform strength.

An electrical magnet can be used instead of a magnet to modify the magnetic force generated in this delivery device. The magnetism-generating means can be moved to a target position of the individual on a table to allow the pair of magnetism-generating means to move in the X, Y, and Z directions.

The tissue of an individual can be placed in the region of the magnetic field to concentrate the drug in the tissue. Existing metal complexes (drug concentration 5 mg/mL (15 mM)) were injected into mice weighing about 30 g, a laparotomy was performed, and the mouse was placed on the iron plate to allow the right kidney to move between the pair of magnets.

Figure 4:
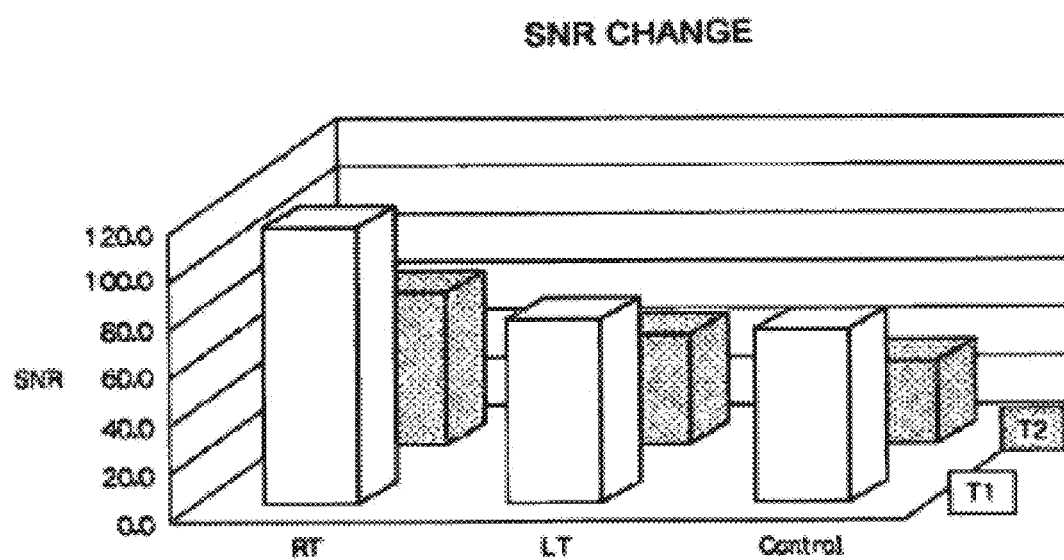
FIG. 4 is a graph of MRI results (T1 enhanced signals) for mouse kidney.

The magnets were Product No. N50 (neodymium permanent magnet) by Shin-Etsu Kagaku Kogyo, with a residual flux density of 1.39 to 1.44 T. At this time, the magnetic field applied to the right kidney was about 0.3 (T), and the field applied to the left kidney was about $\frac{1}{10}$. Together with the left kidney and a kidney to which no field was applied (control), a magnetic field was applied to the right kidney of the mouse, and after 10 minutes the SNR was measured by MRI in T1 mode and T2 mode. As shown in FIG. 4, it was confirmed that the drug stayed in the right kidney (RT) to which the magnetic field was applied, as compared to the left kidney (LT) and control.

Figure 5:
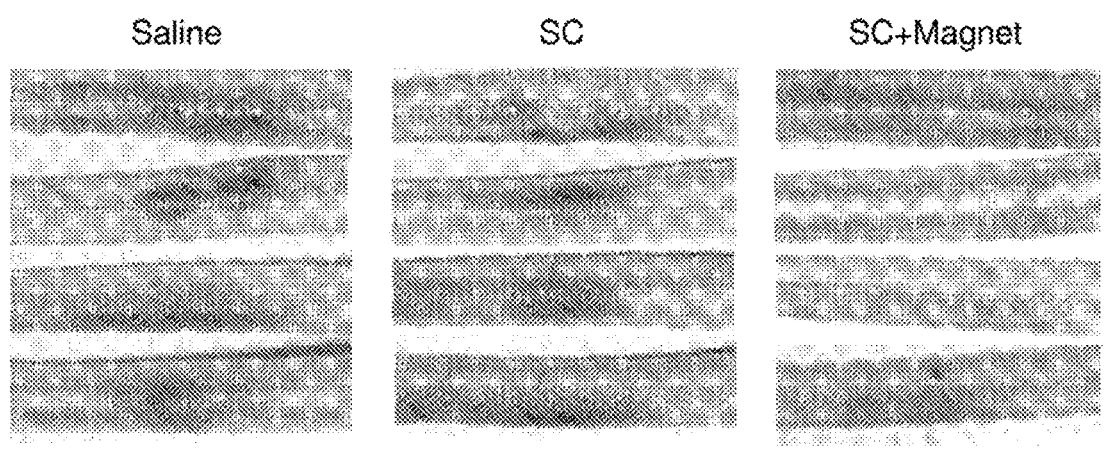
FIG. 5 shows the result of effect of the salen complexes on melanoma growth in mice.
Figure 6:
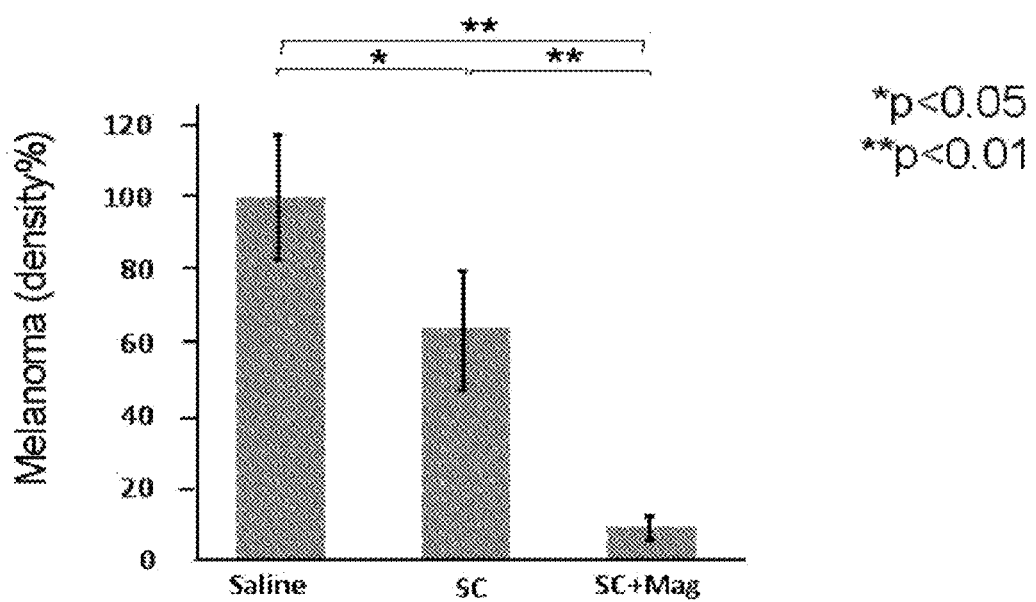
FIG. 6 shows the result of melanoma extension.
Figure 7:
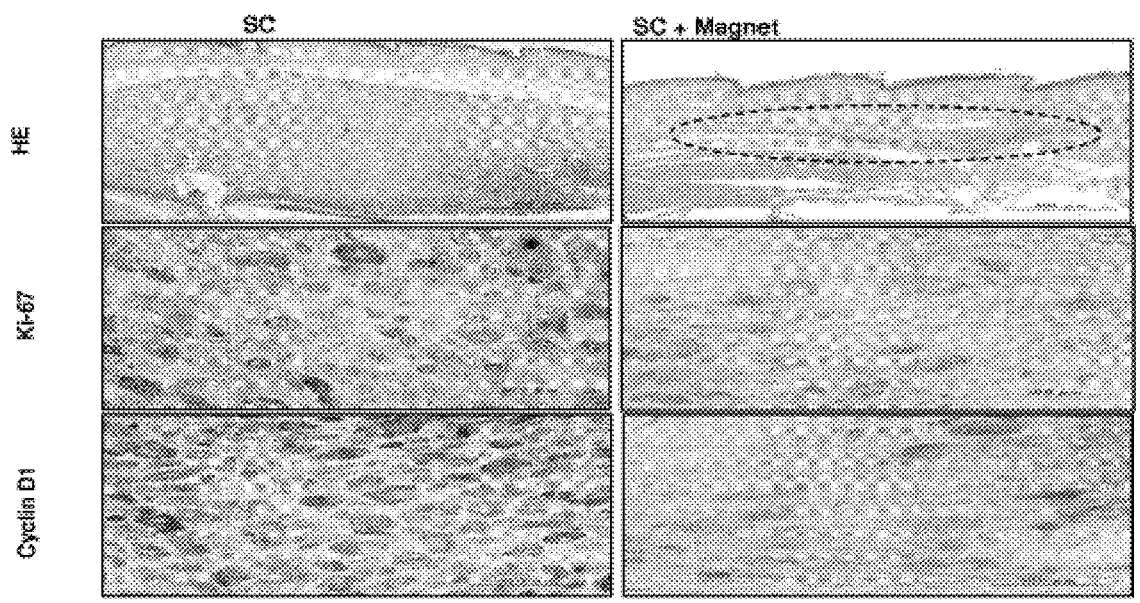
FIG. 7 shows the result of histological examination.

FIG. 5 shows the effect of the salen complexes on melanoma growth in mice. Melanoma was established in mouse tails in vivo by local grafting of cultured melanoma cells (Clone M3 melanoma cells). The salen complex (shown as SC, 50 mg/kg) was administered intravenously via tail vein, followed by local application of a magnetic field by the use of a commercially available bar magnet (630 mT, a cylindrical neodymium magnet, 150 mm in depth and 20 mm in diameter). Application of a bar magnet was performed with 3 hour gentle touch to the site of melanoma immediately after injection of the salen complex for 10-14 days. Application was performed in such a way so that the magnetic field strength became maximal over the area of expected melanoma extension, which was approximately ~150 mm in a mouse tail with the growth period of 2 weeks. Twelve days after the initial injection of the salen complex, the extension of melanoma was evaluated by assessing the area of melanoma pigmentation. As shown in FIG. 6 the melanoma extension was greatest in the saline group (100±17.2%), in which saline, instead of the salen complex, was injected, while it was modestly decreased (63.68±16.3%) in the SC group, in which the salen complex was injected without the application of a magnetic force field. In contrast, melanoma was mostly disappeared (9.05±3.42%) in the SC+magnet group, in which the salen complex was injected and a magnet force field was applied as described above (n=7-10). Histological examination (FIG. 7), as determined by Hematoxylin-Eosin staining and immuno-histochemical staining with an anti-Ki-67 antibody and an anti-Cyclyn D1 antibody, which are both tumor proliferation markers, in tissue sections, revealed that tumor expansion of melanoma was diminished when the salen complex was injected, and was mostly disappeared when the magnetic force field application was combined with the salen complex.

Figure 8:
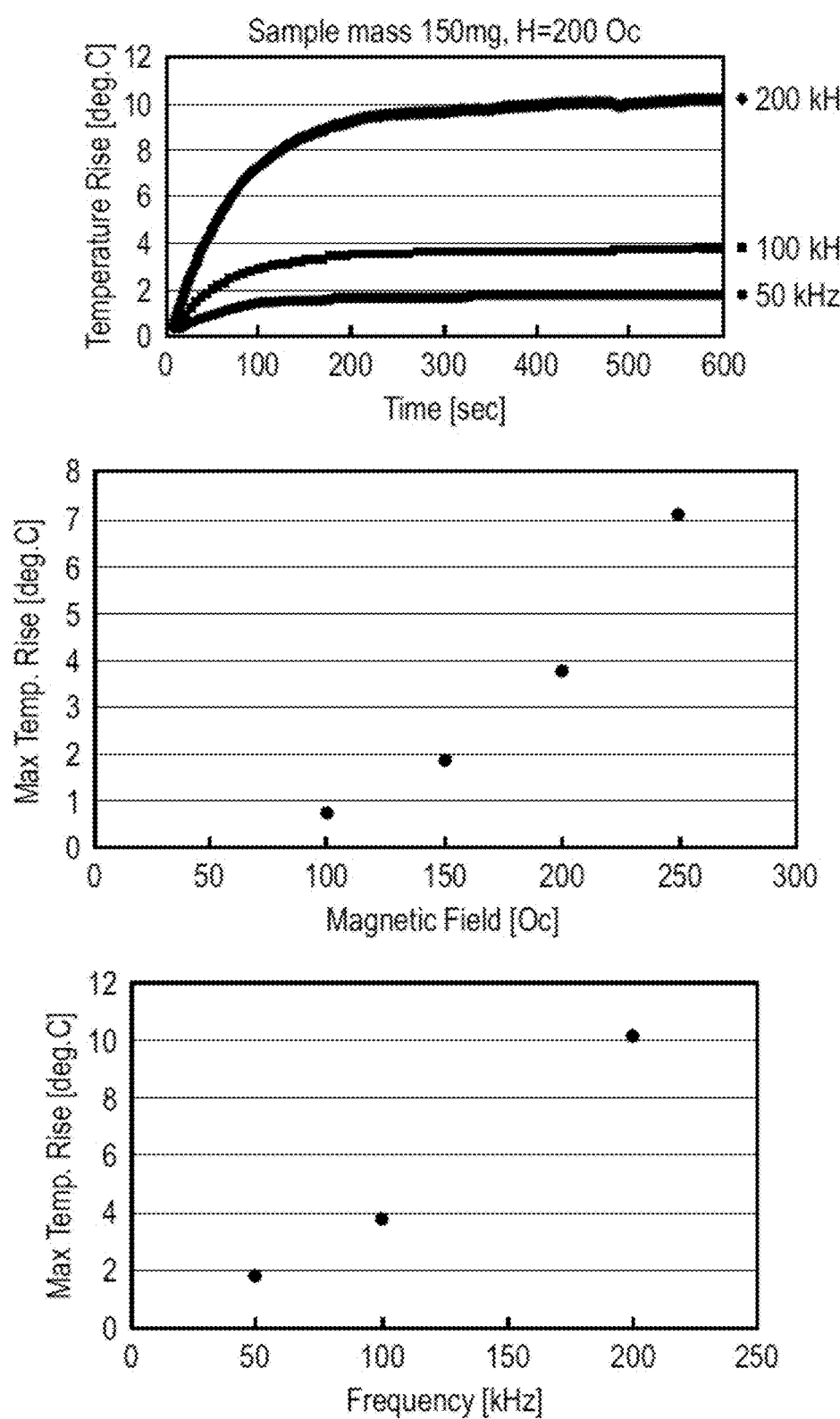
FIG. 8 is a graph of the increase in temperature when an AC magnetic field is applied to the drug.

The application of an AC magnetic field with a field intensity of 200 Oe (Oersted) and a frequency of 50 kHz to 200 kHz to the drug increased the drug temperature from 2° C. to 10° C. (FIG. 8). This confirmed that the temperature zone allowed cells to be killed from 39° C. to 47° C., as calculated in terms of temperature during administration to the living body.

We claim:

1. A method for treating a tumor comprising:
   administering into an individual a composition comprising an iron-salen complex selected from the group consisting of: Formula (I) and Formula (II);

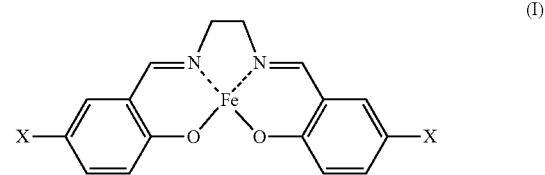

wherein X in Formula (I) is a hydrogen,

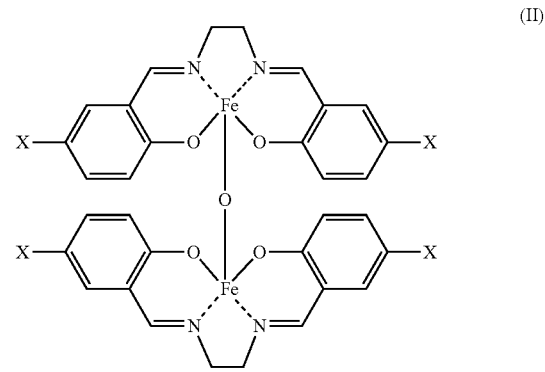

wherein X in Formula (II) is a hydrogen, and
applying a magnetic field to an area of the individual comprising the tumor, thereby delivering the iron-salen complex to the area, wherein the tumor is reduced subsequent to application of the magnetic field to the area.

SEQUENCE LISTING

<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
agcggttcgt aggca                                                    15

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
agcgtattcg gtagc                                                    15

2. The method for treating a tumor according to claim 1, wherein the iron-salen complex is represented by Formula (II).

3. The method for treating a tumor according to claim 1, wherein the iron-salen complex is represented by Formula (I).

4. A method for treating cancer cells, comprising:
administering into an individual a composition comprising an iron-salen complex selected from the group consisting of: Formula (I) and Formula (II);

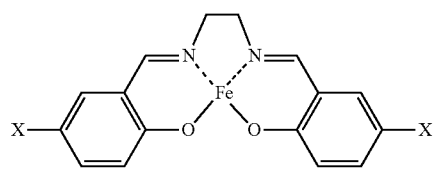
(I)

wherein X in Formula (I) is hydrogen,

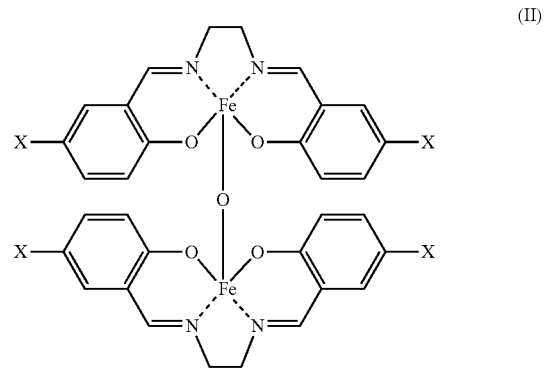
(II)

wherein X in Formula (II) is hydrogen, and
increasing a temperature of the iron-salen complex at least 2° C. by applying a magnetic field to an area of the individual comprising cancer cells, and
destroying the cancer cells due to increasing the temperature of the iron-salen complex.

* * * * *